US00PP26221P2

(12) United States Plant Patent
Arts

(10) Patent No.: US PP26,221 P2
(45) Date of Patent: Dec. 15, 2015

(54) ***HYDRANGEA* PLANT NAMED 'H213901'**

(50) Latin Name: *Hydrangea macrophylla*
Varietal Denomination: H213901

(71) Applicant: Niels Arts, Aalsmeer (NL)

(72) Inventor: Niels Arts, Aalsmeer (NL)

(73) Assignee: Hydrangea Breeders Association B.V., De Kwakel (NL)

( * ) Notice: Subject to any disclaimer, the term of this patent is extended or adjusted under 35 U.S.C. 154(b) by 40 days.

(21) Appl. No.: 13/999,835

(22) Filed: Mar. 27, 2014

(51) Int. Cl.
*A01H 5/00* (2006.01)

(52) U.S. Cl.
USPC ..... Plt./250

(58) Field of Classification Search
USPC ..... Plt./250
CPC ..... A01H 5/02; A01H 5/00
See application file for complete search history.

*Primary Examiner* — Kent L Bell
(74) *Attorney, Agent, or Firm* — C. A. Whealy

(57) ABSTRACT

A new and distinct cultivar of *Hydrangea* plant named 'H213901', characterized by its upright and somewhat outwardly spreading plant habit; vigorous growth habit; freely branching habit; strong and sturdy stems; freely and uniformly flowering habit; and mophead-type inflorescences with numerous dark red purple-colored sterile flowers with undulate margins and apices.

1 Drawing Sheet

Botanical designation: *Hydrangea macrophylla.*
Cultivar denomination: 'H213901'.

BACKGROUND OF THE INVENTION

The present invention relates to a new and distinct cultivar of *Hydrangea* plant, botanically known as *Hydrangea macrophylla*, commercially referred to as a mophead-type *Hydrangea* and hereinafter referred to by the name 'H213901'.

The new *Hydrangea* plant is a product of a planned breeding program conducted by the Inventor in De Kwakel, The Netherlands and Glandorf, Germany. The objective of the breeding program was to create new freely-branching *Hydrangea* plants with strong sturdy stems, large inflorescences, attractive flower color and good postproduction longevity.

The new *Hydrangea* plant originated from a cross-pollination made by the Inventor in April, 2008 in De Kwakel, The Netherlands, of a proprietary selection of *Hydrangea macrophylla* identified as code number 05-0122-080, not patented, as the female, or seed, parent with a proprietary selection of *Hydrangea macrophylla* identified as code number 01-0186-046, not patented, as the male, or pollen, parent. The new *Hydrangea* plant was discovered and selected by the Inventor as a single flowering plant from within the progeny of the stated cross-pollination in a controlled greenhouse environment in Glandorf, Germany in May, 2010.

Asexual reproduction of the new *Hydrangea* plant by vegetative cuttings in a controlled environment in Glandorf, Germany since June, 2010 has shown that the unique features of this new *Hydrangea* plant are stable and reproduced true to type in successive generations.

SUMMARY OF THE INVENTION

Plants of the new *Hydrangea* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'H213901'. These characteristics in combination distinguish 'H213901' as a new and distinct *Hydrangea* plant:

1. Upright and somewhat outwardly spreading plant habit.
2. Vigorous growth habit; freely branching habit.
3. Strong and sturdy stems.
4. Freely and uniformly flowering habit.
5. Mophead-type inflorescences with numerous dark red purple-colored sterile flowers with undulate margins and apices.

Plants of the new *Hydrangea* can be compared to plants of the female parent selection. Plants of the new *Hydrangea* differ primarily from plants of female parent selection in growth habit as plants of the new *Hydrangea* are more compact than plants of the female parent selection. In addition, plants of the new *Hydrangea* and female parent selection differ in sterile flower sepal color as sterile flowers of plants of the female parent selection have pink-colored sepals.

Plants of the new *Hydrangea* can be compared to plants of the male parent selection. Plants of the new *Hydrangea* differ primarily from plants of male parent selection in sterile flower sepal orientation as sepals of sterile flowers of the male parent selection do not have undulate margins and apices.

Plants of the new *Hydrangea* can be compared to plants of the *Hydrangea hybrida* 'Agrihydrazestien', disclosed in U.S. Plant Pat. No. 23,841. In side-by-side comparisons conducted in De Kwakel, The Netherlands, plants of the new *Hydrangea* differed from plants of 'Agrihydrazestien' in the following characteristics:

1. Inflorescences of plants of the new *Hydrangea* were more flattened than and not as globular as inflorescences of plants of 'Agrihydrazestien'.
2. Plants of the new *Hydrangea* had larger sterile flowers than plants of 'Agrihydrazestien'.

3. Plants of the new *Hydrangea* and 'Agrihydrazestien' differed in sterile flower orientation as sterile flowers of plants of 'Agrihydrazestien' did not have undulate margins and apices.
4. Plants of the new *Hydrangea* and 'Agrihydrazestien' differed in sterile flower sepal color as sterile flowers of plants of 'Agrihydrazestien' had dark pink-colored sepals.

BRIEF DESCRIPTION OF THE PHOTOGRAPHS

The accompanying colored photographs illustrate the unique appearance of the new *Hydrangea* plant showing the colors as true as it is reasonably possible to obtain in colored reproductions of this type. Colors in the photographs may differ from the color values cited in the detailed botanical description which accurately describe the colors of the new *Hydrangea* plant.

The photograph at the top of the sheet comprises a side perspective view of a typical flowering plant of 'H213901' grown in a container.

The photograph at the bottom of the sheet is a close-up view of a typical inflorescence of 'H213901'.

DETAILED BOTANICAL DESCRIPTION

Plants used in the aforementioned photographs and in the following description were grown during the summer in 13-cm containers in a glass-covered greenhouse in De Kwakel, The Netherlands and under cultural practices typical of commercial *Hydrangea* production. During the production of the plants, day and night temperatures averaged 17° C. Plants of the new *Hydrangea* were one year old when the photograph and description were taken. In the following description, color references are made to The Royal Horticultural Society Colour Chart, 1995 Edition, except where general terms of ordinary dictionary significance are used.

Botanical description: *Hydrangea macrophylla* 'H213901'.

Parentage:

*Female, or seed, parent*.—Proprietary selection of *Hydrangea macrophylla* identified as code number 05-0122-080, not patented.

*Male, or pollen, parent*.—Proprietary selection of *Hydrangea macrophylla* identified as code number 01-0186-046, not patented.

Propagation:

*Type cutting*.—By vegetative cuttings.

*Time to initiate roots, summer*.—About two weeks at temperatures about 23° C.

*Time to initiate roots, winter*.—About 18 days at temperatures about 18° C.

*Time to produce a rooted young plant, summer*.—About four weeks at temperatures about 23° C.

*Time to produce a rooted young plant, winter*.—About five weeks at temperatures about 18° C.

*Root description*.—Thick; whitish brown in color.

*Rooting habit*.—Freely branching; dense.

Plant description:

*Plant and growth habit*.—Upright and somewhat outwardly spreading plant habit; rounded in shape; strong and sturdy stems; rapid growth rate and vigorous growth habit.

*Plant height*.—About 25 cm to 40 cm.

*Plant diameter or area of spread*.—About 40 cm to 60 cm.

Lateral branch description:

*Branching habit*.—Freely branching habit with about five to six lateral branches per plant.

*Length*.—About 20 cm to 25 cm.

*Diameter*.—About 5 mm to 6 mm.

*Internode length*.—About 3 cm to 4 cm.

*Stem texture*.—Smooth, glabrous.

*Strength*.—Strong, sturdy.

*Color*.—Close to 147C, overlain with close to 187C; lenticels, close to 187D; woody stems, close to 177C.

Leaf description:

*Arrangement*.—Opposite, simple.

*Length*.—About 8 cm to 10 cm.

*Width*.—About 6.5 cm to 7 cm.

*Shape*.—Ovate.

*Apex*.—Acute.

*Base*.—Obtuse.

*Margin*.—Dentate to serrate.

*Texture, upper surface*.—Smooth to rugose, glabrous.

*Texture, lower surface*.—Rugose, glabrous.

*Venation pattern*.—Pinnate.

*Color*.—Developing leaves, upper surface: Close to 139A. Developing leaves, lower surface: Close to 137D. Fully expanded leaves, upper surface: Close to 139B; venation, close to 145B. Fully expanded leaves, lower surface: Close to 137C; venation, close to 145C.

*Petioles*.—Length: About 2 cm. Diameter: About 5 mm. Texture, upper and lower surfaces: Smooth, glabrous. Color, upper and lower surfaces: Close to 145C.

Flower description:

*Flower type and habit*.—Showy sterile flowers and small, inconspicuous star-shaped fertile flowers arranged on mophead-type terminal panicles; panicles flattened globular in shape; flowers face upright to mostly outwardly.

*Fragrance*.—None detected.

*Natural flowering season*.—Plants begin flowering about three months after planting; short production time as a cooling treatment is not required for flower development; continuous flowering during throughout the summer in Northern Europe.

*Flower longevity*.—Sterile flowers last about four months on the plant, sterile flowers persistent; fertile flowers last about one month on the plant, fertile flowers not persistent.

*Quantity of flowers*.—Freely flowering habit; about 60 sterile flowers per panicle and about 30 to 50 fertile flowers per panicle.

*Panicle height*.—About 5 cm to 6 cm.

*Panicle diameter*.—About 15 cm to 17 cm.

*Sterile flower buds*.—Length: About 3 mm. Diameter: About 3 mm. Shape: Spherical. Color: Close to 145C.

*Fertile flower buds*.—Length: About 3 mm. Diameter: About 3 mm. Shape: Spherical. Color: Close to 145C.

*Sterile flower diameter*.—About 4 cm to 5 cm.

*Sterile flower depth (height)*.—About 1.5 cm.

*Fertile flower diameter*.—About 6 mm to 8 mm.

*Fertile flower depth (height)*.—About 6 mm to 8 mm.

*Petals, fertile flowers only, sterile flowers without petals*.—Quantity and arrangement: Five in a single whorl. Length: About 5 mm. Width: About 3 mm. Shape: Ovate. Apex: Obtuse. Base: Cuneate. Margin: Entire. Texture, upper and lower surfaces: Smooth, glabrous. Color: When opening, upper and lower surfaces: Close to 145B. Fully opened, upper and lower surfaces: Close to 73B; color does not change with development.

*Sepals, sterile flowers*.—Quantity and arrangement: Four in a single whorl. Length: About 2 cm to 2.5 cm. Width: About 2.5 cm. Shape: Roughly deltoid. Apex: Acute; undulate. Base: Cuneate. Margin: Entire; undulate. Texture, upper surface: Smooth to slightly rippled, glabrous. Texture, lower surface: Smooth, glabrous. Color: When opening, upper surface: Close to 145C. When opening, lower surface: Close to 145D. Fully opened, upper surface: Close to 57A; under acidic soil conditions, color becomes closer to 89C. Fully opened, lower surface: Close to 68B; under acidic soil conditions, color becomes closer to 91A.

*Sepals, fertile flowers*.—Quantity and arrangement: Five in a single whorl. Length: About 3 mm. Width: About 3 mm. Shape: Ovate. Apex: Acute. Base: Obtuse. Margin: Entire. Texture, upper and lower surfaces: Smooth, glabrous. Color: When opening, upper and lower surfaces: Close to 145B. Fully opened, upper and lower surfaces: Close to 145D; color does not change with development.

*Pedicels, sterile flowers*.—Length: About 3 cm to 3.5 cm. Diameter: About 2 mm. Strength: Strong. Texture: Smooth, glabrous. Color: Close to 57C.

*Pedicels, fertile flowers*.—Length: About 5 mm to 10 mm. Diameter: About 1 mm. Strength: Strong. Texture: Smooth, glabrous. Color: Close to 63D.

*Reproductive organs, fertile flowers only; sterile flowers without reproductive organs*.—Stamens: Quantity per flower: Eight. Filament length: About 1 mm. Filament color: Close to 69B. Anther shape: Conical. Anther length: About 1 mm. Anther color: Close to 155C. Pollen amount: Abundant. Pollen color: Close to 155D. Pistils: Pistil quantity per flower: Three. Pistil length: About 3 mm. Stigma shape: Oval. Stigma color: Close to 69B. Style length: About 1 mm. Style color: Close to 69B. Ovary color: Close to 69C.

*Seeds*.—Quantity per flower: About 20 to 30. Length: About 0.5 mm. Diameter: About 0.1 mm. Color: Close to 200C.

Disease & pest resistance: Under commercial production conditions, plants of the new *Hydrangea* have not been observed to be resistant to pathogens and pests common to *Hydrangea* plants.

Temperature tolerance: Plants of the new *Hydrangea* have been shown to be tolerant to temperatures ranging from about 3° C. to about 38° C.

It is claimed:

1. A new and distinct *Hydrangea* plant named 'H213901' as illustrated and described.

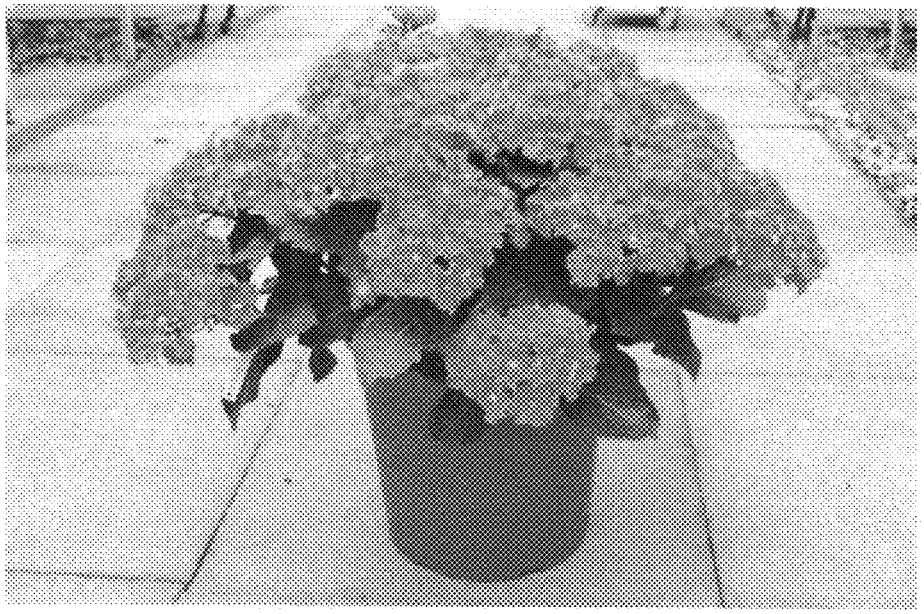
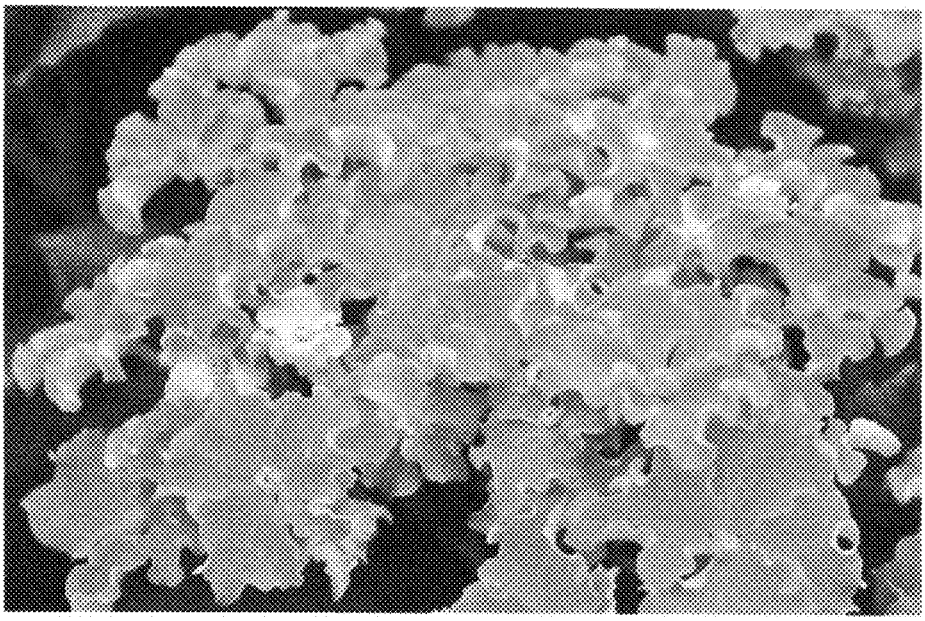

* * * * *